United States Patent
Jones

(10) Patent No.: US 9,566,388 B1
(45) Date of Patent: Feb. 14, 2017

(54) SYRINGE MEASUREMENT MARKING AND DOSING SYSTEM

(71) Applicant: Corey Dewayne Jones, Lavon, TX (US)

(72) Inventor: Corey Dewayne Jones, Lavon, TX (US)

(*) Notice: Subject to any disclaimer, the term of this patent is extended or adjusted under 35 U.S.C. 154(b) by 0 days.

(21) Appl. No.: 15/090,782

(22) Filed: Apr. 5, 2016

(51) Int. Cl.
*A61M 5/315* (2006.01)
*A61D 7/00* (2006.01)
*A61M 5/31* (2006.01)
*A61J 7/00* (2006.01)

(52) U.S. Cl.
CPC ............ *A61M 5/31511* (2013.01); *A61D 7/00* (2013.01); *A61J 7/0053* (2013.01); *A61M 2005/3126* (2013.01); *A61M 2205/584* (2013.01); *A61M 2205/6009* (2013.01); *A61M 2205/6081* (2013.01)

(58) Field of Classification Search
CPC ........ A61M 5/178; A61M 5/31; A61M 5/315; A61M 5/31511; A61M 5/31525; A61M 2005/3114; A61M 2005/3125; A61M 2005/3126; A61M 2205/58; A61M 2205/583; A61M 2205/584; A61M 2205/585; A61M 2205/6009; A61M 2205/6081; A61D 7/00; A61J 7/0053
See application file for complete search history.

(56) References Cited

U.S. PATENT DOCUMENTS

| 2,860,635 A | * | 11/1958 | Wilburn | .................. A61M 5/28 206/365 |
|---|---|---|---|---|
| 6,413,241 B1 | | 7/2002 | Slishman | |
| 7,857,138 B2 | * | 12/2010 | Temple | ..................... A61J 7/04 206/571 |
| 2004/0024368 A1 | | 2/2004 | Broselow | |
| 2007/0221722 A1 | * | 9/2007 | Wayne | ..................... G06G 1/06 235/61 B |
| 2008/0306438 A1 | * | 12/2008 | Ferrara | ................. A61J 1/2096 604/78 |
| 2010/0130961 A1 | | 5/2010 | Tucker | |
| 2013/0204225 A1 | * | 8/2013 | Creaturo | ............. A61M 5/3129 604/506 |
| 2014/0207079 A1 | | 7/2014 | Creaturo | |

* cited by examiner

*Primary Examiner* — Kami A Bosworth
(74) *Attorney, Agent, or Firm* — Jackson Walker LLP

(57) ABSTRACT

A syringe measurement marking system for use with a syringe that includes a barrel and a plunger is marked with patient-based numerical measuring indicia on the plunger. The patient-based numerical measuring indicia is non-volumetric in nature and instead indicates patient dosing criteria such as weight, age, height, blood sugar level, or any other patient criteria by which dosing is determined. The plunger may contain more than one set of patient-based numerical measuring indicia, such as one set for adults or one set for pediatrics, or one set for a first dose of a medication and one set for a second dose, or one set based on weight in pounds and one set based on weight in kilograms. The syringe barrel will contain one or more measurement lines.

16 Claims, 8 Drawing Sheets

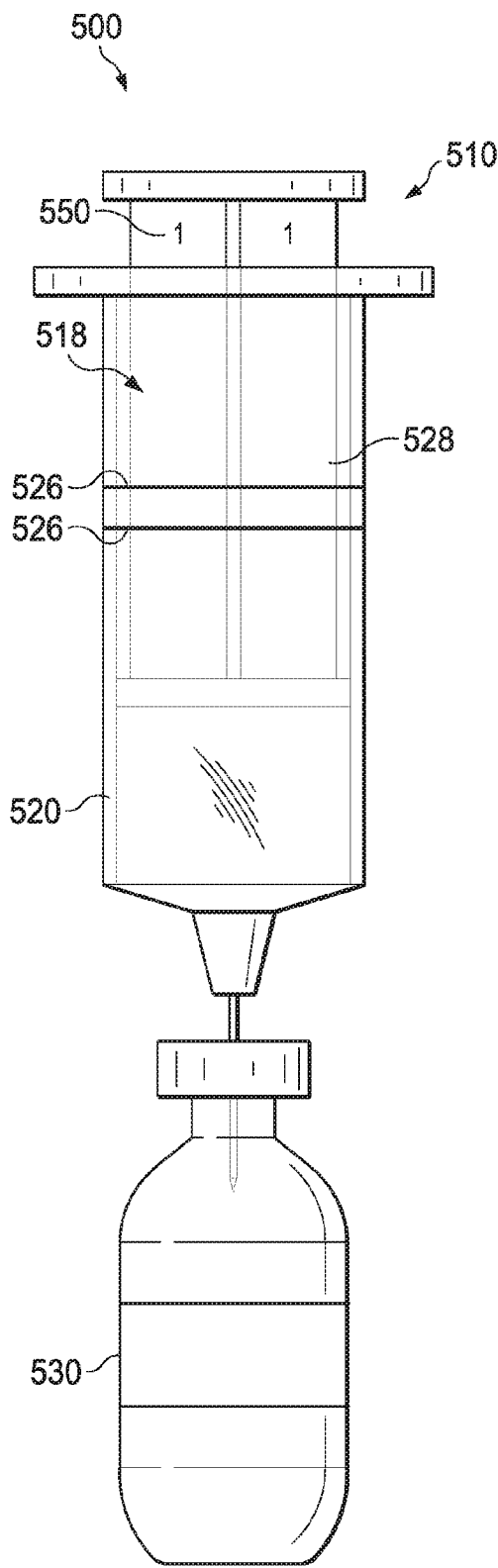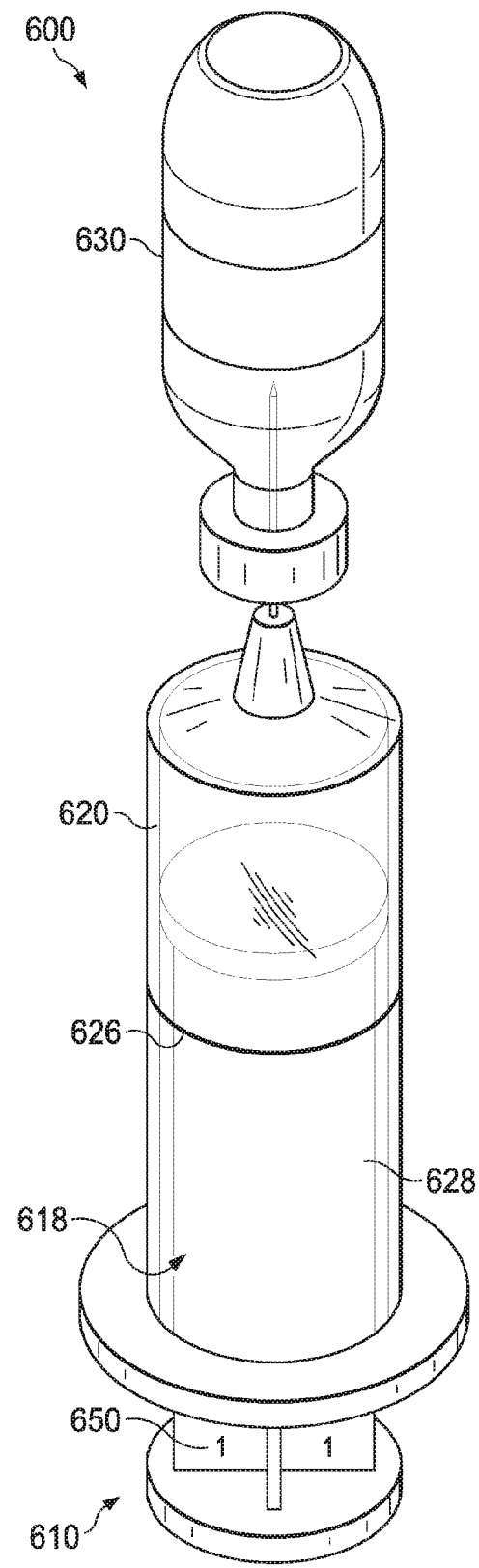
FIG. 5
FIG. 6

US 9,566,388 B1

SYRINGE MEASUREMENT MARKING AND DOSING SYSTEM

FIELD OF THE INVENTION

The present invention pertains to the field of syringes and the measurement and dosing of liquid medication.

BACKGROUND OF THE INVENTION

Syringes are used universally for the measurement, dosing, and administration of liquid medicine. For a variety of reasons, incorrect dosing of liquid medicine using syringes remains a common problem that leads to serious and avoidable consequences.

SUMMARY OF THE INVENTION

The present disclosure pertains to a syringe containing at least one set of patient-based measuring and dosing indicia.

In accordance with an exemplary embodiment of the present disclosure, a syringe that includes a barrel and a plunger is marked with patient-based measuring and dosing indicators on the plunger. The plunger may either be a cross type plunger or a round type plunger. Numbers indicating dosage specific for a patient are included on the plunger rather than the barrel. The patient-based numerical measuring indicia is non-volumetric in nature and instead indicates patient dosing criteria such as weight, age, height, blood sugar level, or any other patient criteria by which dosing is determined. The patient-based measuring indicia is correlated with a specific medication and dosage, which is also preferably indicated on the syringe plunger in proximity to the numerical measuring indicia.

In preferred embodiments, the plunger may contain more than one set of patient-based numerical measuring indicia, such as one set for adults or one set for pediatrics, or one set for a first dose of a medication and one set for a second dose, or one set based on weight in pounds and one set based on weight in kilograms. The orientation of the numerical measuring indicia can be reversed depending on whether the medication will be measured with the barrel and plunger pointed upward or the barrel and plunger pointed downward. In preferred embodiments, for some oral medications, multiple different plungers containing numerical measuring indicia for different medications may be used with a single syringe barrel. In additional preferred embodiments, the plunger or the numerical measuring indicia may be color-coded for ease of reference, such as blue for adult dosages and pink for pediatric dosages. In preferred embodiments, the syringe barrel will contain one or more measurement lines that may be two parallel lines which will line up on either side of the selected numerical indicia of the barrel, or a single line which will bisect the selected numerical indicia. In additional preferred embodiments, the syringe barrel will continue to be marked with standard volumetric measurement and dosing indicia.

The patient-based measurement and dosing indicia of the present disclosure provides a simplified dosing system that eliminates steps in the dosing calculation process and thereby reduces potential dosing errors. Liquid medication is measured and dosed directly with reference to the patient, with no need for any volumetric calculations. Further, including numerical measuring indicia on the plunger rather than the barrel eliminates the confusing intersection of lines and markings present when viewing a transparent syringe barrel, that can also lead to incorrect dosing.

Those skilled in the art will further appreciate the advantages and superior features of the invention together with other important aspects thereof on reading the detailed description that follows in conjunction with the drawings.

BRIEF DESCRIPTION OF THE DRAWINGS

FIG. 5 is a side view of a syringe that is part of a patient-based syringe measurement marking system, in accordance with an exemplary embodiment of the present disclosure;

FIG. 6 is a side perspective view of a syringe that is part of a patient-based syringe measurement marking system, in accordance with an exemplary embodiment of the present disclosure;

DETAILED DESCRIPTION OF PREFERRED EMBODIMENTS

Figure 1A:
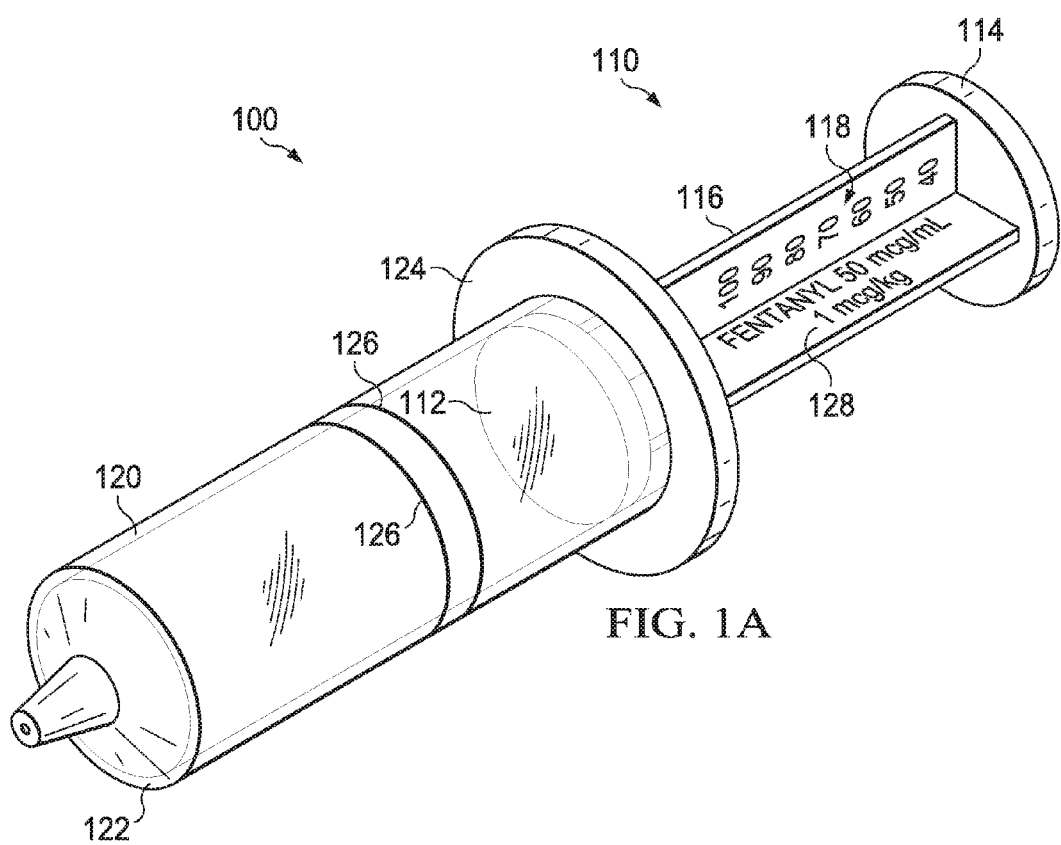
FIG. 1A is a side perspective view of a syringe utilizing a patient-based numerical measuring indicia in accordance with an exemplary embodiment of the present disclosure.

In the description that follows, like parts are marked throughout the specification and drawings with the same reference numerals. The drawing figures might not be to scale and certain components can be shown in generalized or schematic form and identified by commercial designations in the interest of clarity and conciseness.

Figure 1B:
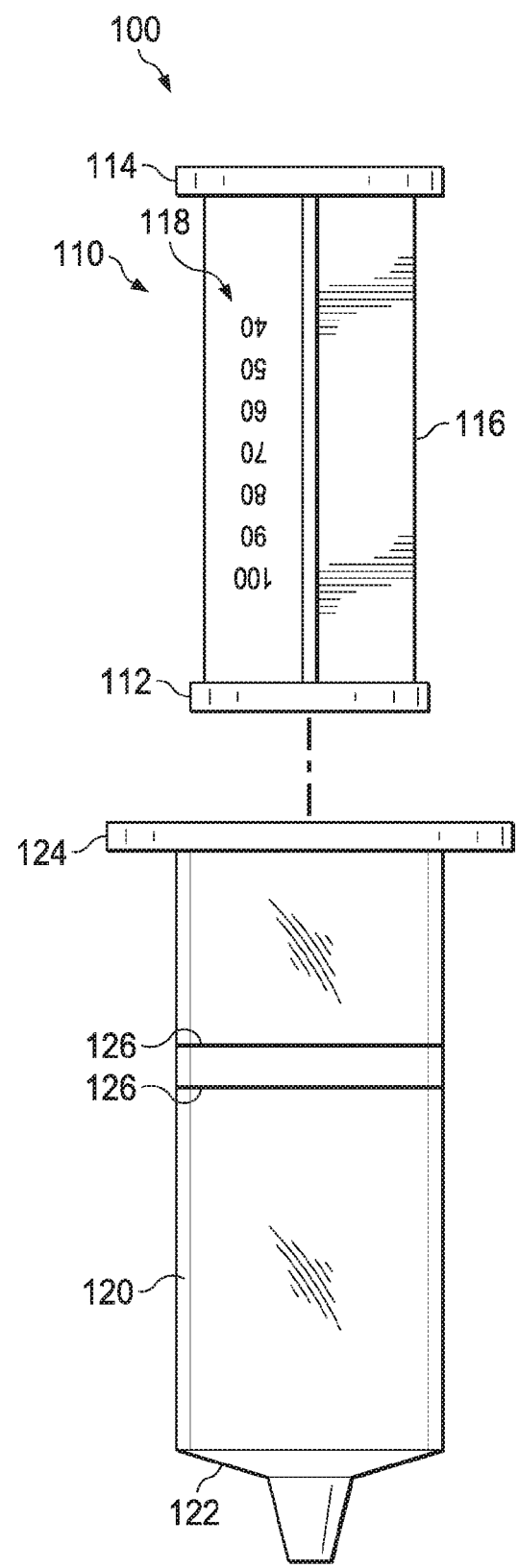
FIG. 1B is a side view of a plunger and barrel of a syringe utilizing a patient-based numerical measuring indicia in accordance with an exemplary embodiment of the present disclosure.

FIG. 1A is a side perspective view of a syringe 100 utilizing a patient-based measuring indicia in accordance with an exemplary embodiment of the present disclosure. Syringe 100 includes a barrel 120 having a top, open end 124 and a bottom, closed end 122. Syringe 100 also includes a cross style plunger 110 having a top end 114, a bottom end 112, and four blades 116 (all four blades not explicitly shown) that make up the "cross" of the plunger. Barrel 120 is marked with two measurement lines 126 in accordance with this embodiment. FIG. 1B is a side view of plunger 110 and barrel 120 of syringe 100. Plunger 110 contains a set of patient-based numerical measuring indicia 118 that represents, in accordance with this embodiment, a range of weight in kilograms for an adult patient. Plunger 110 also contains a dosing label 128 that includes, in this embodiment, the name of the medication (e.g., Fentanyl), the concentration of medication (e.g., 50 mcg/ml), and the dosing of medication that is applicable to the set of numerical measuring indicia 118 (e.g., 1 mcg/kg). As shown in this embodiment, the set of patient-based numerical measuring indicia 118 is oriented to measure the medication when the syringe 100 is pointing upward or in an upright fashion, as most medical professionals measure liquid medication from a vial. In all embodiments, regardless of the orientation of the set of patient-based numerical measuring indicia 118, the largest number (resulting in the largest dosage) will be found near the bottom end 112 of the plunger 110.

Utilizing the embodiment of the patient-based measuring indicia shown in FIGS. 1A AND 1B, an individual such as a medical professional who wishes to administer a dose of medication to a patient, such as 1 mcg/kg of Fentanyl from a vial of Fentanyl having a concentration of 50 mcg/ml, simply needs to obtain the applicable syringe and plunger containing this dosing label and to know the weight in kilograms of the patient. If the patient weighs 80 kilograms, then the medical professional simply has to place the syringe in the vial of Fentanyl having the concentration noted on the plunger (e.g., 50 mcg/ml), then line up the number "80" found on the set of patient-based numerical measuring indicia 118 on plunger 110 between the measurement lines 126 on barrel 120 to obtain the correct amount of Fentanyl for administration. This eliminates the step of having to calculate the volume based on the correct dosing (e.g., 1 mcg/kg), the patient's weight (e.g., 80 kg), and the concentration of medication in the vial (e.g., 50 mcg/ml). The measurement lines 126 are calibrated in a fashion that provides the appropriate quantity or dose of liquid medicine corresponding to the selected weight, even though the medicine is not drawn from the vial with direct reference to volume.

In additional preferred embodiments, the set of patient-based numerical measuring indicia 118 illustrated in FIG. 1 may be any range of patient-based dosing criteria in any units and in any increments. Accordingly, the set of patient-based numerical measuring indicia may be a range of adult patient weights in pounds or kilograms, or a range of pediatric patient weights in pounds or kilograms. The numerical measuring indicia may indicate a range of patient heights or ages. In certain preferred embodiments, the numerical measuring indicia may be increments of patient blood sugar (e.g., 50 mg/dL) that are above the patient's target blood sugar level (e.g., 150 mg/dL). The patient may administer one unit of insulin for each increment that he or she is above the target blood sugar level. As there are many ways in which a patient may administer insulin, the indicia used on the plunger may be changed accordingly. In each preferred embodiment, a dosing label 128 similar to that shown in FIG. 1 is found in proximity to the numerical measuring indicia to indicate the applicable medication, concentration, and dosing. In certain preferred embodiments, the syringe may be packaged with the medication it is intended for use with and the plunger may not require a label showing the concentration or other associated dosing information.

Figure 2A:
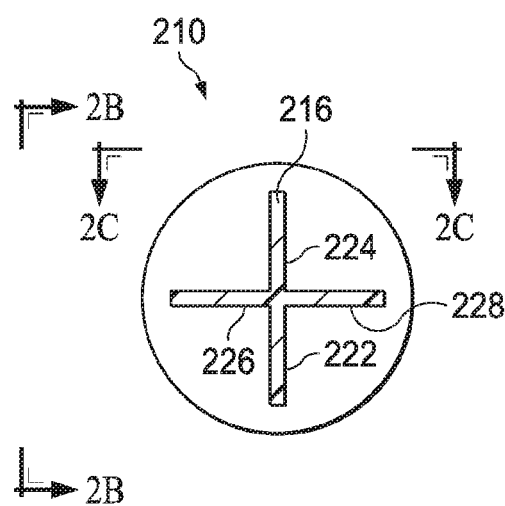
FIG. 2A is a partial top view of a cross style plunger that is part of a patient-based syringe measurement marking system, in accordance with an exemplary embodiment of the present disclosure.
Figure 2B:
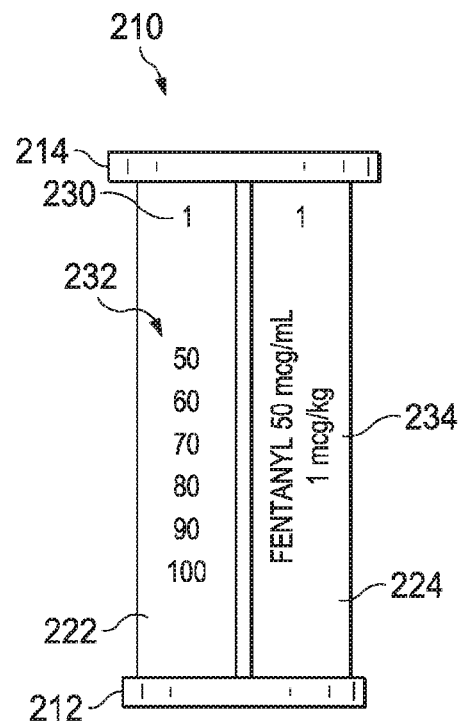
FIG. 2B is a side view of a cross style plunger that is part of a patient-based syringe measurement marking system, in accordance with an exemplary embodiment of the present disclosure.
Figure 2C:
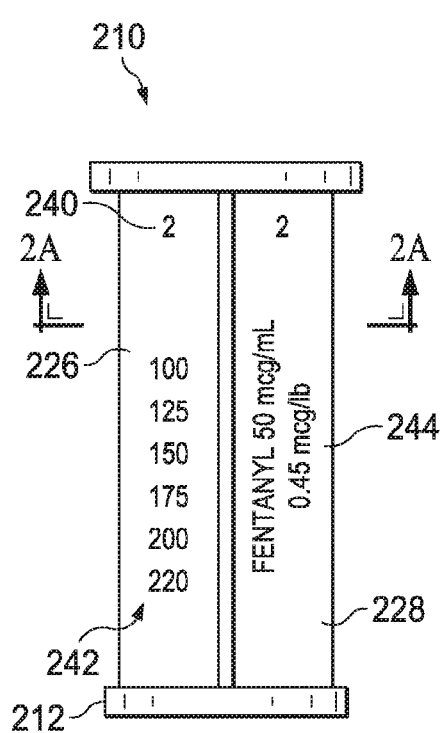
FIG. 2C is an alternate side view of a cross style plunger that is part of a patient-based syringe measurement marking system, in accordance with an exemplary embodiment of the present disclosure.

FIG. 2A is a partial top view of a cross style plunger 210 that is part of a patient-based syringe measuring system 200 that includes four blades 216 that make up the cross, in accordance with an embodiment of the present disclosure. It can be seen from FIG. 2A that there are eight possible surfaces on blades 216 that can be marked with suitable measuring and dosing indicia, including surfaces 222, 224, 226, and 228. FIG. 2B is a side view of plunger 210 in which, in this particular embodiment, surfaces 222 and 224 contain a set of patient-based numerical measuring indicia 232 and a dosing label 234. In the embodiment shown in FIG. 2B, the set of patient-based numerical measuring indicia 232 is a range of patient weight in kilograms and dosing label 234 refers to the medication Fentanyl at a concentration 50 mcg/mL and a dosage of 1 mcg/kg, but any suitable patient-based numerical measuring indicia may be used to reflect any suitable patient criteria. Surfaces 222 and 224 also include marker 230 which ensures that the user is referring to the correct numerical measuring indicia for the particular dosing label. In this embodiment, marker 230 is the number "1" for both the set of patient-based numerical measuring indicia 232 and the dosing label 234. As shown in FIG. 2C, which is also a side view of plunger 210, marker 240 is the number "2" for both the set of patient-based numerical measuring indicia 242 found on surface 226 and the dosage label 244 found on surface 228. The set of patient-based numerical measuring indicia 242 is a range of patient weight in pounds and dosing label 244 is the medical Fentanyl at a concentration 50 mcg/mL and a dosage of 0.45 mcg/lb. As seen in FIG. 2A, the two measuring and dosing schemes shown in FIGS. 2B and 2C can be present on the same plunger 210 and used with the same medication. The measuring system 200 provides flexibility to the user in the event the patient's weight is available in either kilograms or pounds. It can be seen on plunger 210 that the largest patient weight is found toward the bottom end 212 of plunger 210 in either set of patient-based numerical measuring indicia, while the smallest patient weight is found toward the top end 214 of plunger 210. The sets of patient-based numerical measuring indicia 232 and 242 are both oriented such that the plunger 210 is used with a syringe pointing downward to measure the medication.

Figure 3A:
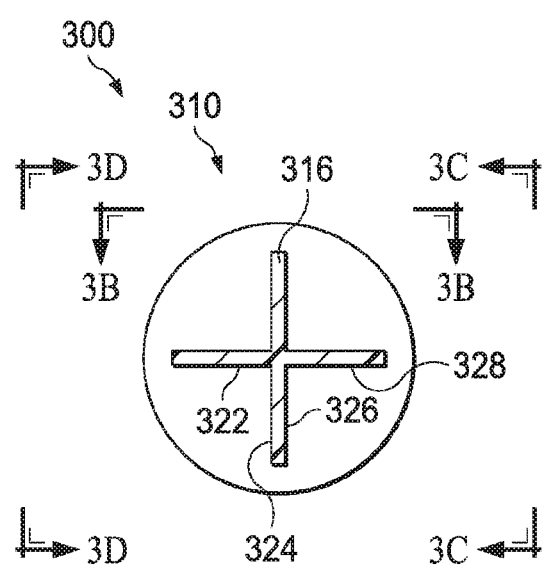
FIG. 3A is a partial top view of a cross style plunger that is part of a patient-based syringe measurement marking system, in accordance with an exemplary embodiment of the present disclosure.
Figure 3B:
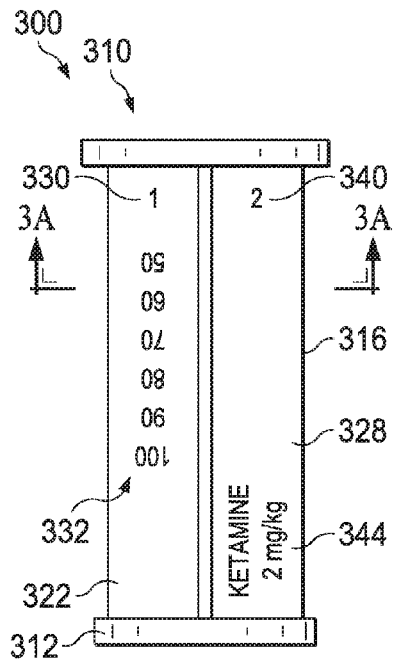
FIG. 3B is a side view of a cross style plunger that is part of a patient-based syringe measurement marking system, in accordance with an exemplary embodiment of the present disclosure.
Figure 3C:
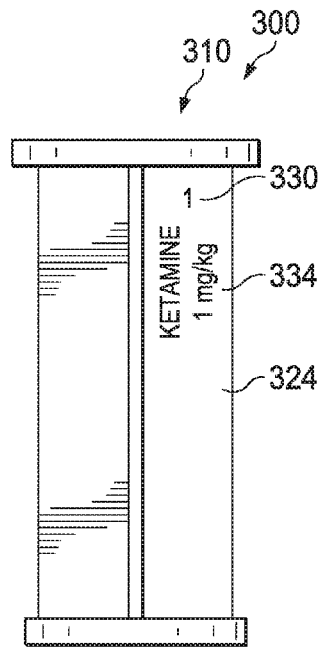
FIG. 3C is an alternate side view of a cross style plunger that is part of a patient-based syringe measurement marking system, in accordance with an exemplary embodiment of the present disclosure.
Figure 3D:
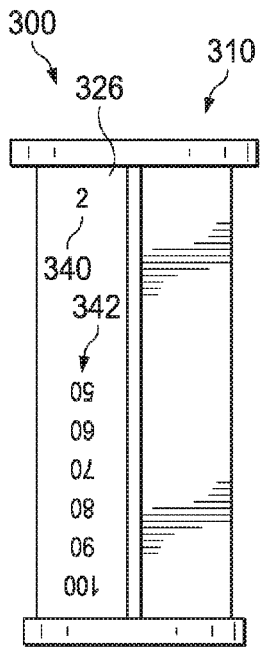
FIG. 3D is an alternate side view of a cross style plunger that is part of a patient-based syringe measurement marking system, in accordance with an exemplary embodiment of the present disclosure.

FIG. 3A is a partial top view of a cross style plunger 310 that is part of a patient-based syringe measuring system 300 that includes four blades 316 that make up the cross, in accordance with an embodiment of the present disclosure. It can be seen from FIG. 3A that there are eight possible surfaces on blades 316 that can be marked with suitable measuring and dosing indicia, including surfaces 322, 324, 326, and 328. FIGS. 3B, 3C, and 3D are side views of plunger 310. FIG. 3B is a side view of plunger 310 in which surfaces 322 and 328 contain a set of patient-based numerical measuring indicia 332 and a dosing label 344. In the embodiment shown in FIGS. 3A-3D, the set of patient-based numerical measuring indicia and corresponding dosing labels are on immediately adjacent surfaces. Accordingly, as seen in FIG. 3B, the set of patient-based numerical measuring indicia 332 does not correspond to dosing label 344. The set of patient-based numerical measuring indicia 332 corresponds to dosing label 334 found on surface 324, as seen in FIG. 3C. The set of patient-based numerical measuring indicia 342 found on surface 326, as seen in FIG. 3D, corresponds to dosing label 344 seen in FIG. 3B. In the embodiment shown in FIGS. 3A-3D, the sets of patient-based numerical measuring indicia 332 and 342 are both a range of patient weight in kilograms. However, the numerical measuring indicia correspond to different dosing amounts of the same medication, Ketamine at 2 mg/kg shown in dosing label 344 and Ketamine at 1 mg/kg shown in dosing label 334. Ketamine is typically administered with a first dosage at 2 mg/kg and a second dosage at 1 mg/kg, so this embodiment allows the same plunger to be used for either dosage amount. Surfaces 322 and 324 also include marker 330 which ensures that the user is referring to the correct numerical measuring indicia for the particular dosing label. In this embodiment, marker 330 is the number "1" for both the set of patient-based numerical measuring indicia 332 (FIG. 3B) and the dosing label 334 (FIG. 3C). Marker 340 is the number "2" for both the set of patient-based numerical measuring indicia 342 found on surface 326 (FIG. 3D) and the dosage label 344 found on surface 328 (FIG. 3B). It can be seen on plunger 310 that the largest patient weight is found toward the bottom end 312 of plunger 310 in both sets of patient-based numerical measuring indicia. The sets of patient-based numerical measuring indicia 332 and 342 are both oriented such that the plunger 310 is used with a syringe pointing upward to measure the medication.

Figure 4A:
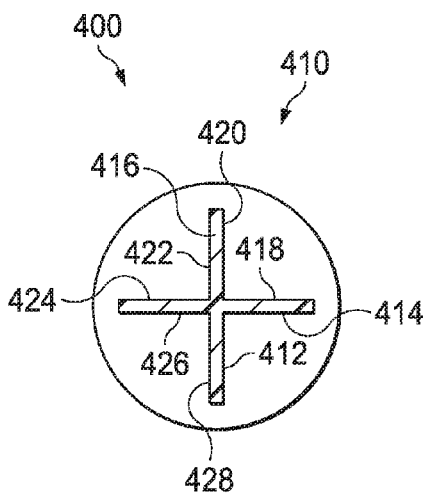
FIG. 4A is a partial top view of a cross style plunger that is part of a patient-based syringe measurement marking system for syringes, in accordance with an exemplary embodiment of the present disclosure.
Figure 4B:
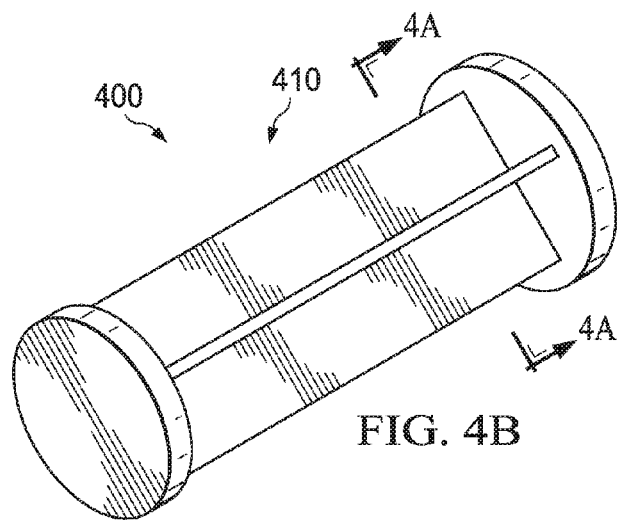
FIG. 4B is a side perspective view of a cross style plunger that is part of a patient-based syringe measurement marking system, in accordance with an exemplary embodiment of the present disclosure.

FIG. 4A is a partial top view of a cross style plunger 410 that is part of a patient-based measuring system for syringes 400, in accordance with a preferred embodiment of the present disclosure. FIG. 4B shows a side perspective view of plunger 410. Plunger 410 includes four blades 416 and eight surfaces—412, 414, 418, 420, 422, 424, 426, and 428—any of which may be labeled with an appropriate set of patient-based numerical measuring indicia (such as a range of patient ages, weights, or blood sugar levels) and an associated dosing label. For example, in a preferred embodiment, surface 412 includes a set of patient-based numerical measuring indicia that is a range of patient weights in kilograms or pounds, and surface 414 may include a dosing label that includes the name of a medication that may be administered by patient weight. The labeling of adjacent surfaces in this manner is also shown in the embodiments illustrated in FIG. 1 and in FIGS. 3A-3D. The rest of surfaces 418, 420, 422, 424, 426, and 428 may be blank or may be labeled with any other suitable measurements or labels.

In an additional preferred embodiment described with reference to FIG. 4A, surface 412 includes a set of patient-based numerical measuring indicia that is a range of patient weights in kilograms, and adjacent surface 414 includes a set of patient-based numerical measuring indicia that is a range of patient weights in pounds. In this embodiment, any other available surface, such as surface 422, could include a dosing label for the medication that is administered according to the numerical measuring indicia. In additional embodiments, each pair of adjacent surfaces 412 and 414, 418 and 420, 422 and 424, and 426 and 428 could each contain on one surface a set of patient-based numerical measuring indicia and on the adjacent surface a dosing label. In this embodiment, a single plunger 410 could contain dosing and measurement information for four different medications. In this embodiment, adjacent surfaces, such as surfaces 412 and 414 or surfaces 418 and 420 might also include a marker such as a number "1" or a letter "A" that ensures that the correct measuring indicia is used with the correct medication.

In a further exemplary embodiment described with reference to FIG. 4A, surfaces 412 and 420 might include a set of patient-based numerical measuring indicia and a dosing label, respectively. A set of corresponding patient-based numerical measuring indicia and dosing label might also be found on surfaces 426 and 414, 418 and 424, and 422 and 428.

FIG. 5 shows an additional exemplary embodiment of a patient-based syringe measurement system 500 in accordance with the present disclosure. Plunger 510 is a cross style plunger including a set of patient-based numerical measuring indicia 518 and a dosing label 528 arranged to be viewed in a side by side fashion when seen through barrel 520. Plunger 510 also includes a marker 550 that is, in this embodiment, the number "1," which associates the set of patient-based numerical measuring indicia 518 with the dosing label 528. Barrel 520 includes measurement lines 526. In the embodiment shown in FIG. 4, measurement lines 526 are lined up around a patient measuring characteristic of 80, which may be a patient weight of 80 kg, to obtain the correct dosing amount. In the embodiment shown in FIG. 5, the set of patient-based numerical measuring indicia are oriented to permit the syringe barrel 520 and plunger 510 to be used in a downward fashion to measure medication from vial 530.

FIG. 6 shows an additional exemplary embodiment of a patient-based syringe measurement system 600 in accordance with the present disclosure. Plunger 610 is a cross style plunger including a set of patient-based numerical measuring indicia 618 and a dosing label 628 arranged to be viewed in a side by side fashion when seen through barrel 620. Plunger 610 also includes a marker 650 that is, in this embodiment, the number "1," which associates the set of patient-based numerical measuring indicia 618 with the dosing label 628. Barrel 620 includes a single measurement line 626. In the embodiment shown in FIG. 6, measurement line 626 bisects a patient measuring characteristic of 100, which may be a patient weight of 100 kg, to obtain the correct dosing amount. In the embodiment shown in FIG. 6, the set of patient-based numerical measuring indicia are oriented to permit the syringe barrel 620 and plunger 610 to be used in an upward or upside down fashion to measure medication from vial 630.

Figure 7A:
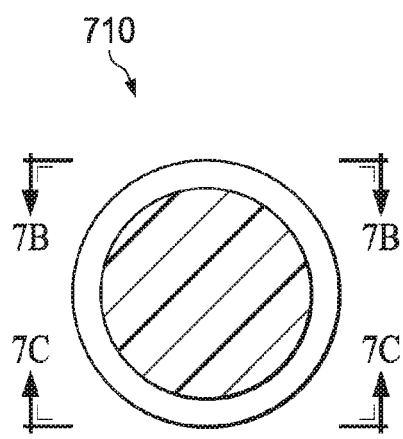
FIG. 7A is a top view of a round style plunger that is part of a patient-based syringe measurement marking system, in accordance with an exemplary embodiment of the present disclosure.
Figure 7D:
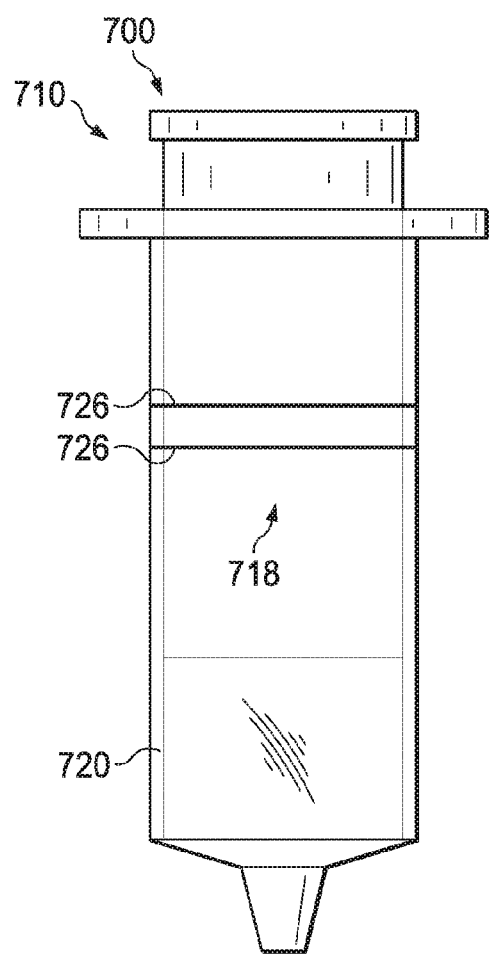
FIG. 7D is a side view of a syringe that is part of a patient-based syringe measurement marking system, in accordance with an exemplary embodiment of the present disclosure.
Figure 7B:
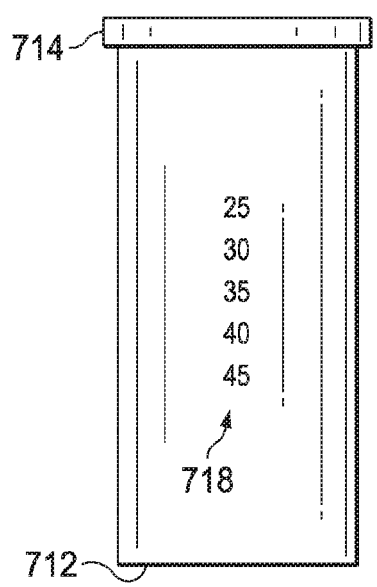
FIG. 7B is a side view of a round style plunger that is part of a patient-based syringe measurement marking system, in accordance with an exemplary embodiment of the present disclosure.
Figure 7C:
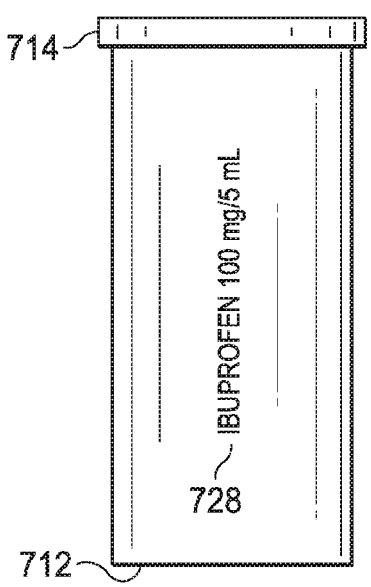
FIG. 7C is an alternate side view of a round style plunger that is part of a patient-based syringe measurement marking system, in accordance with an exemplary embodiment of the present disclosure.

FIG. 7A shows a top view of a plunger 710 that is a round style plunger used in conjunction with a patient-based syringe measuring system 700, in accordance with an exemplary embodiment of the present disclosure. FIG. 7B is a side view of plunger 710 showing a set of patient-based measuring indicia 718 that in this embodiment is a range of pediatric patient weights in pounds. As seen in FIG. 7B, the largest patient-based characteristic, or weight in this embodiment, is located toward the bottom end 712 of plunger 710 while the smaller patient-based characteristic, or weight in this embodiment, is located toward the top end 714 of plunger 710. FIG. 7C is a side view of plunger 710 showing a dosing label 728 that corresponds to the set of patient-based measuring indicia 718 seen in FIG. 7B. In this embodiment, the plunger 710 is used with the medication Ibuprofen at a concentration of 100 mg/5 mL, and dosing is based on the weight of the pediatric patient in pounds. FIG. 7D shows plunger 710 used in combination with barrel 720. Measurement lines 726 found on barrel 720 are lined up around a pediatric patient weight of 40 pounds to obtain the correct dosage. In this embodiment, the set of patient-based numerical measuring indicia 718 are oriented so that plunger 710 and barrel 720 are used to measure the medication in a downward fashion.

Figure 8:
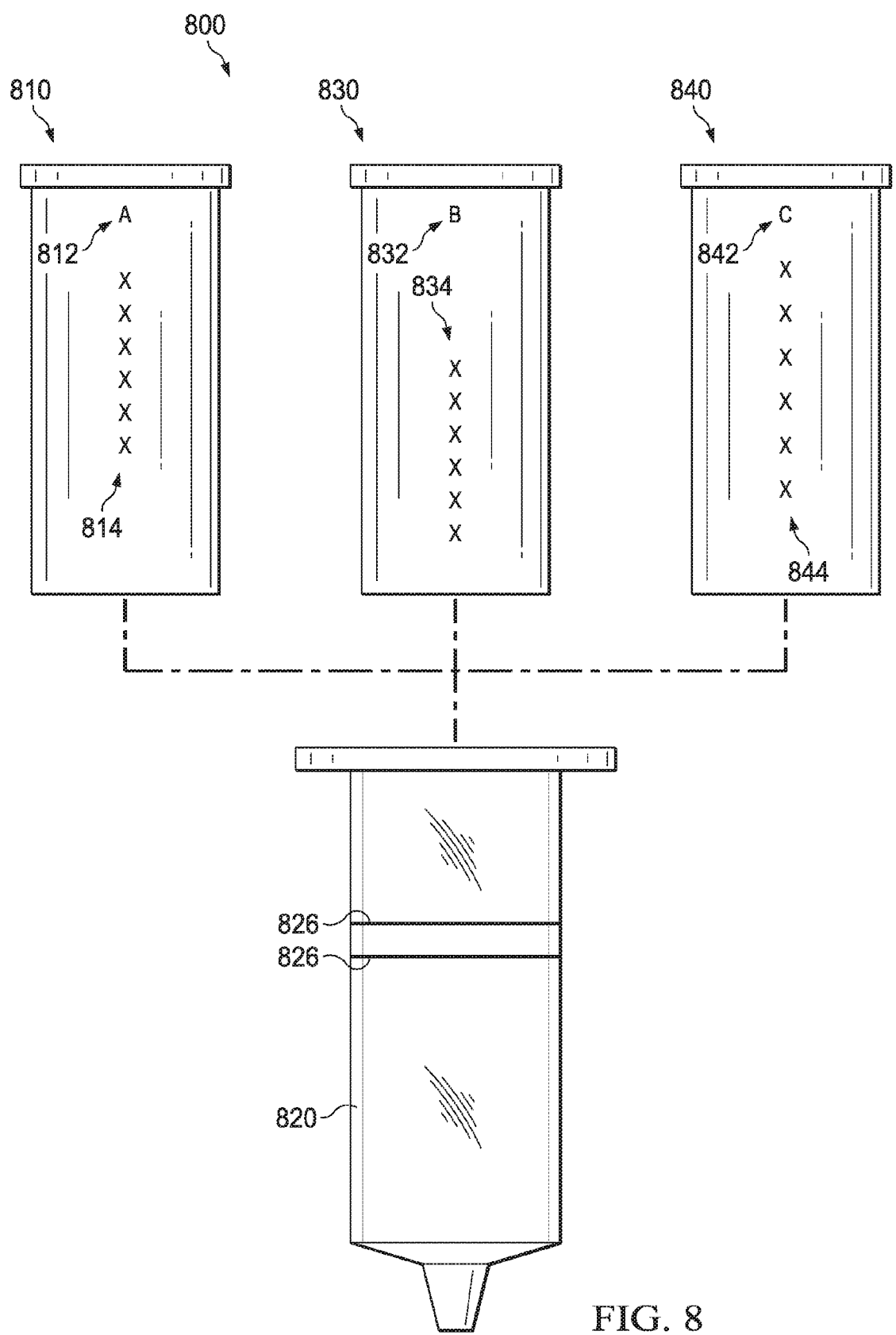
FIG. 8 is a side view of a barrel and round style plungers that are part of a patient-based syringe measurement marking system, in accordance with an exemplary embodiment of the present disclosure.

FIG. 8 shows a patient-based syringe measurement system 800 that includes a barrel 820 having measurement lines 826 and multiple swappable plungers 810, 830, and 840. In this embodiment, plungers 810, 830, and 840 are all round type plungers and each contains a marker 812, 832, and 842, respectively, which is associated with a particular medication. Markers 812, 832, and 842 in this embodiment are letters, such as "A," "B," and "C," but they may be any label which correctly associates the measuring indicia with the correct medication. Plungers 810, 830, and 840 each include a set of patient-based numerical measuring indicia 814, 834, and 844 that are specific to the particular associated medication, such as age or weight. On the reverse side of plungers 810, 830, and 840 (not explicitly shown), the name of the medication could also be provided, along with suitable information on concentration and/or dosing, as desired. Swappable plungers 810, 830, and 840 are preferably used with oral medications in which syringe barrel 820 may be reused. Examples of these medications include any over-the-counter oral children's medicines.

The patient-based syringe measurement and dosing system described herein is useful for both laypeople and medical professionals and may be used in veterinary applications as well. All sizes and styles of syringes and plungers may be used in conjunction with the patient-based syringe measurement and dosing system. In additional exemplary embodiments, color coding may be used to associate a particular set of patient-based numerical measuring indicia with a particular medication and dosing. For example, red numbers may be used on a plunger for a set of patient-based numerical measuring indicia, and red letters may be used on the same plunger for the medication that is associated with that set of measuring indicia. Thus, in FIG. 1, measuring indicia 118 and dosing label 128 may be printed in the same color. In FIG. 2B, measuring indicia 232 and dosing label 234 may be printed in the same color, while measuring indicia 242 and dosing label 244 may be printed in a different color. The color blue may be used for adult dosages, while the color pink may be used for pediatric dosages. Similarly, in a preferred embodiment using swappable plungers such as that shown in FIG. 8, each plunger may be a different color. Plungers may be colored blue for use with adult dosages and pink for use with pediatric dosages.

Figure 9:
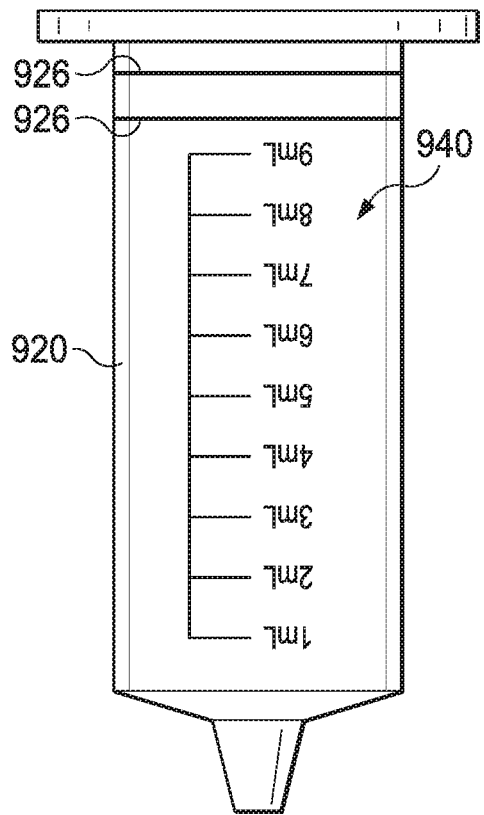
FIG. 9 is a side view of a barrel that is part of a patient-based syringe measurement marking system, in accordance with an exemplary embodiment of the present disclosure.

FIG. 9 shows an exemplary embodiment of a syringe barrel 920 that may be used in conjunction with the patient-based syringe measuring and dosing system described herein. In this embodiment, barrel 920 continues to include typical, standard volumetric measurement markings 940 but also includes measurement lines 926, enabling barrel 920 to be used in conjunction with any of the plungers described herein that utilize the patient-based numerical measuring indicia.

Figure 10:
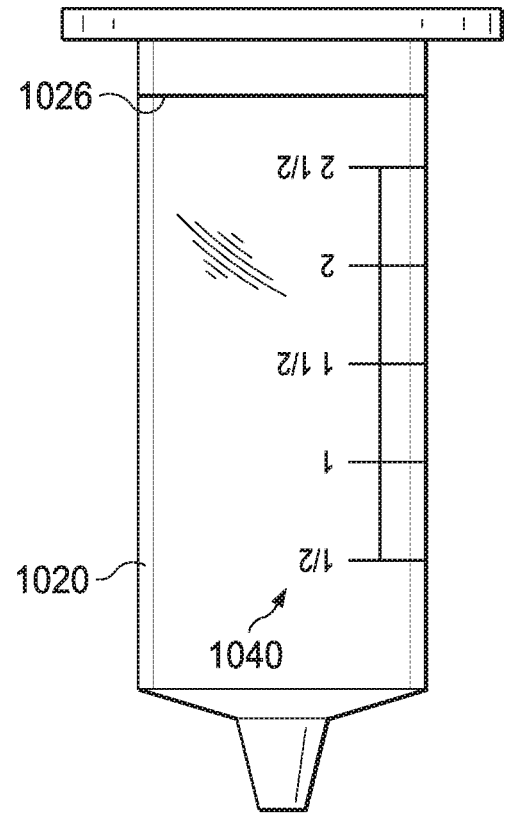
FIG. 10 is a side view of a barrel that is part of a patient-based syringe measurement marking system, in accordance with an exemplary embodiment of the present disclosure.

FIG. 10 shows an exemplary embodiment of a syringe barrel 1020 that may be used in conjunction with the patient-based syringe measuring and dosing system described herein. In this embodiment, barrel 1020 continues to include typical, standard volumetric measurement markings 1040 but also includes measurement line 1026, enabling barrel 1020 to be used in conjunction with any of the plungers described herein that utilize the patient-based numerical measuring indicia. The barrels 920 and 1020 shown in the embodiments of FIGS. 9 and 10 would be useful for anyone interested in double-checking the accuracy of the patient-based syringe measurement marking system described herein.

Although exemplary embodiments of a system and method of the present invention have been described in detail herein, those skilled in the art will also recognize that various substitutions and modifications can be made to the systems and methods without departing from the scope and spirit of the appended claims.

What is claimed is:

1. A patient-based syringe measurement marking system for a syringe including a barrel and at least one plunger for use in dispensing liquid medication, comprising:

a first set of patient-based numerical measuring indicia located on a plunger of the syringe, wherein the first set of patient-based numerical measuring indicia is a range of numbers used for measurement and dosing of liquid medication that is non-volumetric and based on a patient criteria;

a second set of patient-based numerical measuring indicia located on the plunger of the syringe, wherein the second set of patient-based numerical measuring indicia is a range of numbers used for measurement and dosing of liquid medication that is non-volumetric and based on a patient criteria;

at least one measurement line located on the barrel of the syringe, wherein the measurement line is calibrated to line up with a selected number in the range of numbers of the first set or the second set of patient-based numerical measuring indicia in order to measure a quantity of the liquid medication that is a correct dose for the selected number and the patient criteria when the plunger is pulled from the barrel of the syringe, and wherein the barrel further comprises standard volumetric measurement markings;

dosing labels identifying one or more of the liquid medication, a concentration of the liquid medication, and a volumetric dosage of the liquid medication corresponding to the first set and the second set of patient-based numerical measuring indicia, wherein each dosing label is located on the plunger in proximity to the corresponding first set or the corresponding second set of patient-based numerical measuring indicia; and markers located on the plunger in proximity to and corresponding to the first set and the second set of patient-based numerical measuring indicia and also located on the plunger in proximity to the dosing labels, wherein each marker identifies a correlation between the corresponding first set or the corresponding second set of patient-based numerical measuring indicia and the corresponding dosing label.

2. The patient-based syringe measurement marking system of claim 1, wherein the first set and the second set of patient-based numerical measuring indicia are oriented to be read when the syringe is used in an upright fashion.

3. The patient-based syringe measurement marking system of claim 1, wherein the first set and the second set of patient-based numerical measuring indicia are oriented to be read when the syringe is used in a downward fashion.

4. The patient-based syringe measurement marking system of claim 1, wherein the patient criteria for each set of patient-based numerical measuring indicia is selected from the list comprising patient weight in pounds, patient weight in kilograms, patient age, patient height, or patient blood sugar level.

5. The patient-based syringe measurement marking system of claim 1, wherein the patient criteria for the first set of patient-based numerical measuring indicia is patient weight, and wherein the first set of patient-based numerical measuring indicia located on the plunger is a range of patient weights in kilograms.

6. The patient-based syringe measurement marking system of claim 5, wherein the second set of patient-based numerical measuring indicia located on the plunger is a range of patient weights in pounds.

7. The patient-based syringe measurement marking system of claim 1, wherein the patient criteria for the first set of patient-based numerical measuring indicia is patient weight, and wherein the first set of patient-based numerical measuring indicia located on the plunger is a range of patient weights that corresponds to a first dose of the liquid medication.

8. The patient-based syringe measurement marking system of claim 7, wherein the second set of patient-based numerical measuring indicia located on the plunger is a range of patient weights that corresponds to an alternative dose of the liquid medication.

9. The patient-based syringe measurement marking system of claim 1, wherein the first set of patient-based numerical measuring indicia located on the plunger corresponds to an adult dose of the liquid medication, and wherein the second set of patient-based numerical measuring indicia located on the plunger corresponds to a pediatric dose of the liquid medication.

10. The patient-based syringe measurement marking system of claim 1, wherein the plunger is a cross-type plunger or a round-type plunger.

11. The patient-based syringe measurement marking system of claim 1, further comprising a plurality of plungers for use with the barrel, wherein each additional plunger comprises at least one set of patient-based numerical measuring indicia corresponding to a liquid medication.

12. The patient-based syringe measurement marking system of claim 11, wherein the liquid medication differs for each plunger.

13. The patient-based syringe measurement marking system of claim 11, wherein each plunger is a different color.

14. The patient-based syringe measurement marking system of claim 1, wherein the first set of patient-based numerical measuring indicia and the second set of patient-based numerical measuring indicia are different colors.

15. The patient-based syringe measurement marking system of claim 14, wherein each dosing label is the same color as the corresponding first set or the corresponding second set of patient-based numerical measuring indicia.

16. The patient-based syringe measurement marking system of claim 1, wherein the patient is a human or an animal.

* * * * *